(12) United States Patent
Buerger et al.

(10) Patent No.: US 10,342,580 B2
(45) Date of Patent: *__Jul. 9, 2019__

(54) BRACKET FOR EXTERNAL FIXATION OF BONES

(71) Applicant: PBD, Patent & Business Development AG, Zug (CH)

(72) Inventors: Heinz Buerger, Klagenfurt (AT); Markus Hirsch, Klagenfurt-Viktring (AT)

(73) Assignee: PBD, Patent & Business Development AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,215

(22) Filed: Feb. 27, 2018

(65) Prior Publication Data

US 2018/0185064 A1 Jul. 5, 2018

Related U.S. Application Data

(63) Continuation-in-part of application No. 15/402,396, filed on Jan. 10, 2017, now Pat. No. 9,936,976.

(60) Provisional application No. 62/301,741, filed on Mar. 1, 2016.

(51) Int. Cl.
*A61B 17/56* (2006.01)
*A61B 17/64* (2006.01)

(52) U.S. Cl.
CPC ........ *A61B 17/645* (2013.01); *A61B 17/6441* (2013.01); *A61B 17/6466* (2013.01); *A61B 2017/564* (2013.01)

(58) Field of Classification Search
CPC ... A61B 17/6441; A61B 17/66; A61B 17/645; A61B 17/6466; A61B 2017/564
See application file for complete search history.

(56) References Cited

U.S. PATENT DOCUMENTS

| 4,488,542 A | 12/1984 | Helland |
| 4,548,199 A | 10/1985 | Agee |
| 4,573,459 A | 3/1986 | Litton |
| 4,724,827 A | 2/1988 | Schenck |
| 4,745,913 A | 5/1988 | Castaman et al. |

(Continued)

FOREIGN PATENT DOCUMENTS

| WO | 2007/095429 A1 | 8/2007 |
| WO | 2008/036016 A1 | 3/2008 |

OTHER PUBLICATIONS

International Search Report and the Written Opinion of the International Searching Authority dated Apr. 25, 2017 in PCT/EP2017/054753.

*Primary Examiner* — Lynnsy M Summitt
*Assistant Examiner* — Tara Rose E Carter
(74) *Attorney, Agent, or Firm* — Collard & Roe, P.C.

(57) ABSTRACT

A fixation system for fixing a bone fracture has a plurality of blocks, needles and rods that snap together in a framework around the fracture. The needles are inserted through the bone and the blocks are snapped onto the ends of the needles. Rods are snapped onto the blocks on both sides of the finger to keep the finger in place. Each block has two channels located on opposite sides and extending perpendicular to each other. The channels are structured so that a rod or needle having a diameter equal or slightly greater than one of the channels can be snapped into and retained by the channel.

9 Claims, 4 Drawing Sheets

(56) References Cited

U.S. PATENT DOCUMENTS

| | | |
|---|---|---|
| 4,895,141 A | 1/1990 | Koeneman et al. |
| 4,978,348 A | 12/1990 | Ilizarov |
| 5,074,865 A | 12/1991 | Fahmy |
| 5,376,091 A | 12/1994 | Hotchkiss et al. |
| 5,437,668 A | 8/1995 | Aronson et al. |
| 5,653,707 A | 8/1997 | Taylor et al. |
| 5,690,633 A | 11/1997 | Taylor et al. |
| 5,707,370 A | 1/1998 | Berki et al. |
| 5,743,898 A | 4/1998 | Bailey et al. |
| 5,746,741 A | 5/1998 | Kraus et al. |
| 5,788,695 A | 8/1998 | Richardson |
| 5,810,814 A | 9/1998 | Newson |
| 5,976,125 A | 11/1999 | Graham |
| 5,976,136 A | 11/1999 | Bailey et al. |
| 6,010,501 A | 1/2000 | Raskin et al. |
| 6,024,745 A | 2/2000 | Faccioli et al. |
| 6,162,223 A | 12/2000 | Orsak et al. |
| 6,277,118 B1 | 8/2001 | Grant et al. |
| 6,491,694 B1 | 12/2002 | Orsak |
| 9,273,715 B2 | 3/2016 | Bordeaux |
| 9,539,029 B1 | 1/2017 | Muniz et al. |
| 9,622,780 B2 | 4/2017 | Gerold et al. |
| 9,622,781 B2 | 4/2017 | Chang |
| 9,936,976 B2 * | 4/2018 | Buerger ............. A61B 17/6425 |
| 2002/0013584 A1 | 1/2002 | Termaten |
| 2003/0187432 A1 | 10/2003 | Johnson et al. |
| 2003/0216734 A1 | 11/2003 | Mingozzi et al. |
| 2003/0216739 A1 | 11/2003 | Ip et al. |
| 2005/0085754 A1 | 4/2005 | Werding et al. |
| 2005/0261680 A1 | 11/2005 | Draper et al. |
| 2006/0155276 A1 | 7/2006 | Walulik et al. |
| 2006/0229605 A1 | 10/2006 | Olsen |
| 2006/0235383 A1 | 10/2006 | Hollawell |
| 2006/0247621 A1 | 11/2006 | Waisman |
| 2007/0038217 A1 | 2/2007 | Brown et al. |
| 2007/0043354 A1 | 2/2007 | Koo et al. |
| 2007/0281283 A1 | 12/2007 | Lundgren |
| 2008/0195095 A1 | 8/2008 | Renard et al. |
| 2009/0024128 A1 | 1/2009 | Nakamura et al. |
| 2009/0054897 A1 | 2/2009 | Gordon et al. |
| 2009/0118733 A1 | 5/2009 | Orsak et al. |
| 2009/0187189 A1 | 7/2009 | Mirza et al. |
| 2009/0287212 A1 | 11/2009 | Hirata et al. |
| 2011/0034924 A1 | 2/2011 | Tan |
| 2012/0150180 A1 | 6/2012 | Verma et al. |
| 2012/0150181 A1 | 6/2012 | Dorawa et al. |
| 2012/0150182 A1 | 6/2012 | Dominik et al. |
| 2012/0150183 A1 | 6/2012 | Dorawa et al. |
| 2012/0253410 A1 | 10/2012 | Taylor et al. |
| 2013/0110110 A1 | 5/2013 | Waisman |
| 2014/0025075 A1 | 1/2014 | Hokanson |
| 2014/0031822 A1 | 1/2014 | Venturini et al. |
| 2014/0275959 A1 | 9/2014 | Disegi et al. |
| 2014/0276815 A1 | 9/2014 | Riccione |
| 2015/0127001 A1 | 5/2015 | Aoki et al. |
| 2015/0308478 A1 | 10/2015 | Oesch et al. |
| 2015/0342643 A1 | 12/2015 | Fitzpatrick |
| 2016/0015426 A1 | 1/2016 | Dayton |
| 2016/0022314 A1 | 1/2016 | Bordeaux et al. |
| 2016/0038185 A1 | 2/2016 | Disegi et al. |
| 2016/0095626 A1 | 4/2016 | Sanders et al. |
| 2016/0249952 A1 | 9/2016 | Gerold et al. |
| 2016/0270822 A1 | 9/2016 | Cresina et al. |
| 2016/0310167 A1 | 10/2016 | Tepic |
| 2016/0367291 A1 | 12/2016 | Erickson et al. |
| 2017/0071633 A1 | 3/2017 | Sanders et al. |
| 2017/0281234 A1 | 10/2017 | Muniz et al. |

* cited by examiner

BRACKET FOR EXTERNAL FIXATION OF BONES

CROSS-REFERENCE TO RELATED APPLICATIONS

This application is a continuation-in-part of U.S. patent application Ser. No. 15/402,396, filed on Jan. 10, 2017, which claims priority under 35 USC 119(e) of U.S. Provisional Application Ser. No. 62/301,741, filed on Mar. 1, 2016, the disclosures of which are herein incorporated by reference.

BACKGROUND OF THE INVENTION

1. Field of the Invention

This invention relates to a bracket for external fixation of broken bones. In particular, this invention relates to a snap-on bracket that can hold the horizontal and vertical rods of the fixation brace in place.

2. The Prior Art

When a bone is fractured and requires fixation, the fixation can take place by attaching rods to the bone fragments to put them in place for healing over time. This fixation can take place internally, such as by a rod running through the bone, or externally, via rods placed alongside the exterior of the limb or digit to be fixed. For complex bone fractures it is often necessary to fix the fractured pieces externally. There are a variety of systems available on the market that allow adjusting of angles and distances, mostly by using screws and bolts. For most fractures, these external fixations are suitable. But there is a problem with fractures of small bones, especially fractured fingers. External fixations for finger fractures are miniaturized systems, also using screws. However, there is in most cases not enough room to use these still too bulky fixations. Many surgeons have resorted to using their own concepts. For example, glues such as bone cement are put in place to create the links between the needles that are shot into the bone and the perpendicular fixation rods. But the glues are difficult to handle and require a lot of preparation time as they are usually 2-component systems. And after the glue has been applied, it takes a few minutes to harden. During this time, the surgeon needs to assure that everything stays in the correct position, which is difficult and time-consuming.

SUMMARY OF THE INVENTION

It is therefore an object of the invention to provide a bracket for attaching the pins or screws extending from the bone fragments to an external rod. It is another object of the invention to provide a fixation system that is simple and inexpensive to use, and is effective for fixing fractures in small bones.

These and other objects are accomplished by a fixation system for fixing a fracture in one or more bones, comprising a plurality of blocks, needles and rods that snap together in a framework around the fracture. The needles are inserted through the bone on opposite sides of the fracture, such that the needles extend entirely through the finger on both sides. The blocks are snapped onto the needles, and then rods are snapped onto the blocks on both sides of the finger to create a rigid framework to keep the finger in place. The needles could also be inserted at different angles to each other or only on one side of the finger.

Each block has a first channel extending in a first direction and being open to a first surface of the block, and a second channel extending in a second direction and being open to a second surface of the block. The first surface and second surface are located opposite each other and the first channel is arranged perpendicular to the second channel. This way the needles and rods can be snapped onto the block on opposite sides of the block so that they extend perpendicular to each other. The channels are structured so that a width of the channel at each of the first and second surfaces is less than a diameter of the channel, so that a rod or needle having a diameter equal or slightly greater than one of the channels can be snapped into and retained within the respective channel.

The first and second channels have different diameters—one channel being dimensioned to hold the needles running through the bones, and the other channel being dimensioned to hold the exterior rods.

The bracket is preferably made of molded polyurethane. The bracket can be manufactured by creating a prototype via 3-D printing, then molding silicon around the prototype in a mold to create a mold cavity in the shape of the desired block. A clip can be fixed over the channels, so that once the needle or rod is in place, the clip can be closed over the channel to lock the needles and/or rods in place.

Generally, the needles are manufactured from surgical steel, titanium or other suitable metal, and the rods can be made of reinforced carbon fiber, which is invisible to X-rays, so that visualization of the fracture is easier.

The system can be used to stabilize the finger on only one side, or can be set up so that the brackets are placed at oblique angles, rather than on opposite sides of the finger. A clip can optionally be used to hold the needles and/or rods in place.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
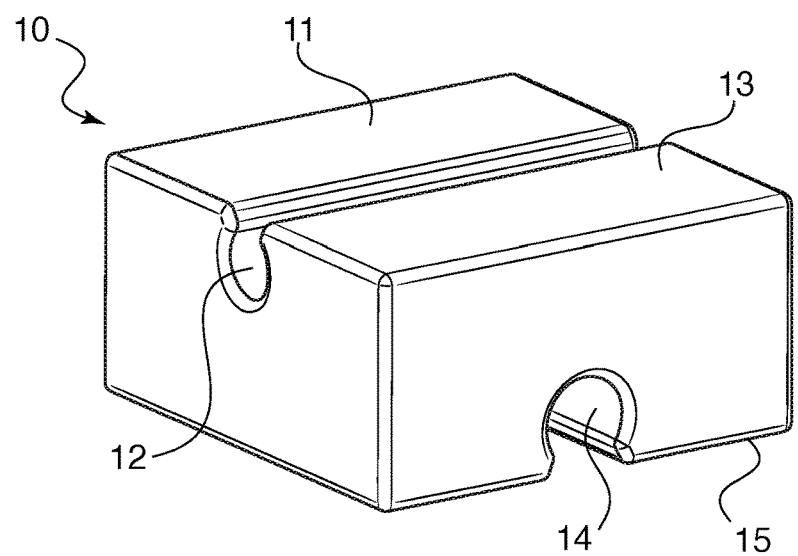
FIG. 1 shows the bracket according to the invention.

Referring now in detail to the drawings, FIG. 1 shows the bracket 10 for use in the system according to the invention. Bracket 10 consists of a block 11 having a first channel 12 located on a first surface 13, and a second channel 14 located on a second surface 15. Surface 13 and surface 15 are located on opposite sides of block 11. Channel 12 and channel 14 extend perpendicular to each other. The shape of channels 12 and 13 is roughly circular, with the opening onto surfaces 13 and 15 being smaller than a diameter of the respective channel. This shape ensures that a needle or rod inserted into the channel is retained in the channel. Block 11 is preferably formed from polyurethane, but other materials could be used. Block 11 is preferably molded and can be manufactured by 3D printing a model, pouring silicone around the model in a mold to create the mold cavity, and then molding the block using polyurethane in the silicone mold. Any other suitable manufacturing methods could be used as well.

Figure 2:
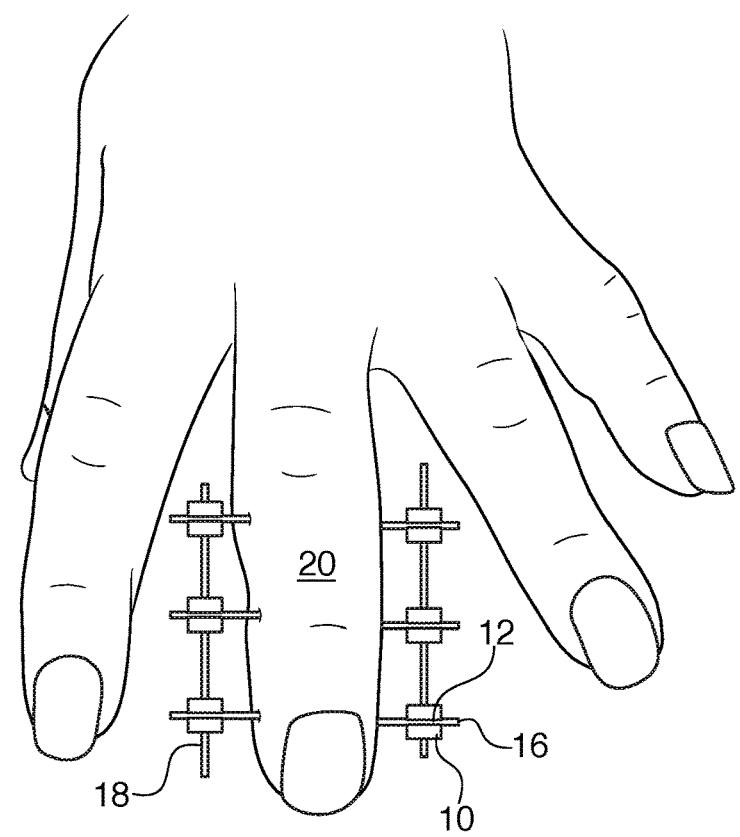
FIG. 2 shows a finger being fixed using the fixation system according to the invention.
Figure 3:
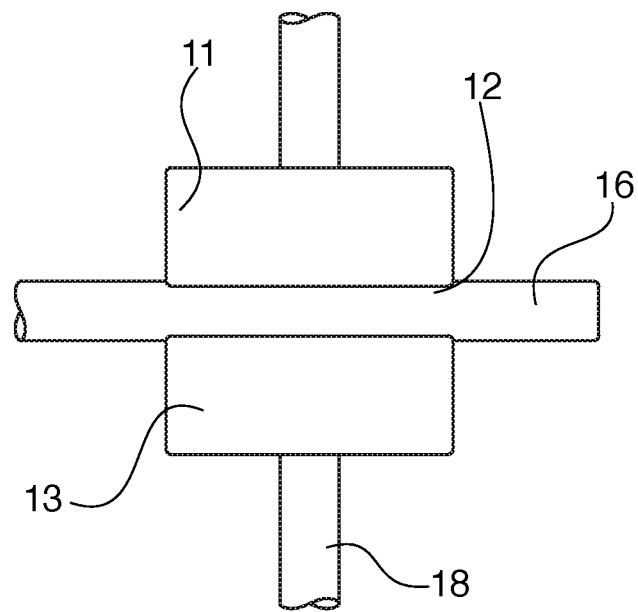
FIG. 3 shows a top view of a bracket according to the invention holding a pin and a rod from the fixation system.
Figure 4:
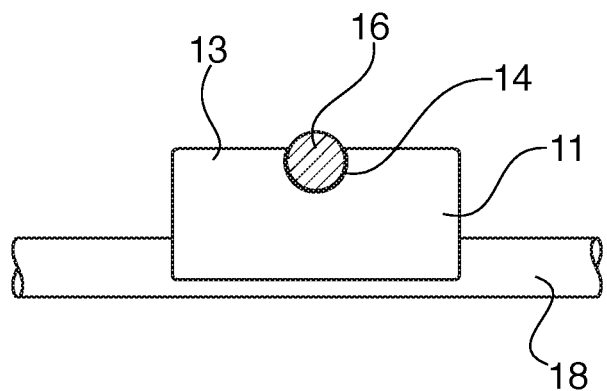
FIG. 4 is a side view of the arrangement of FIG. 3.

FIG. 2 shows a view of the fixation system according to the invention in used on a finger 20. Here, needles 16 are inserted through the bones in the finger and are then attached to brackets 10 by snapping them into channels 14. Glue can also be added for extra stabilization, but is not necessary. Rods 18 are also attached to blocks 10 by snapping them into channels 14. FIGS. 3 and 4 show enlarged views of the rods 18 and needles 16 attached to brackets 10. Preferably, rods 18 and needles 16 have diameters that are just slightly larger than the diameters of channels 14 and 12, respectively, so that the rods and needles are held in the channels with friction fit. The needles are usually a standard size in all hospitals (0.8 mm or 1.0 mm). The rod preferably has a diameter of 1.2 mm. The brackets can be molded with channels of any specified size.

Figure 5:
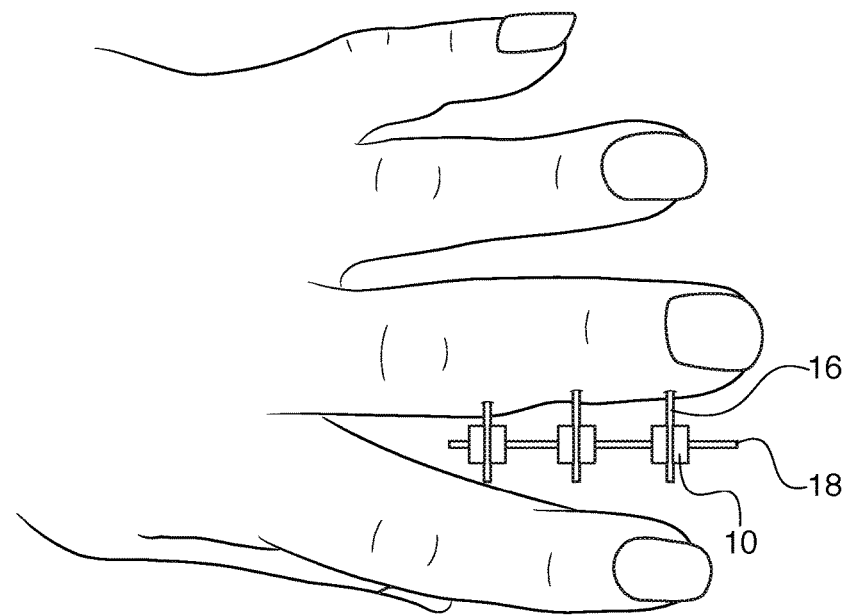
FIG. 5 shows a finger being fixed using the fixation system in an alternative way.
Figure 6:
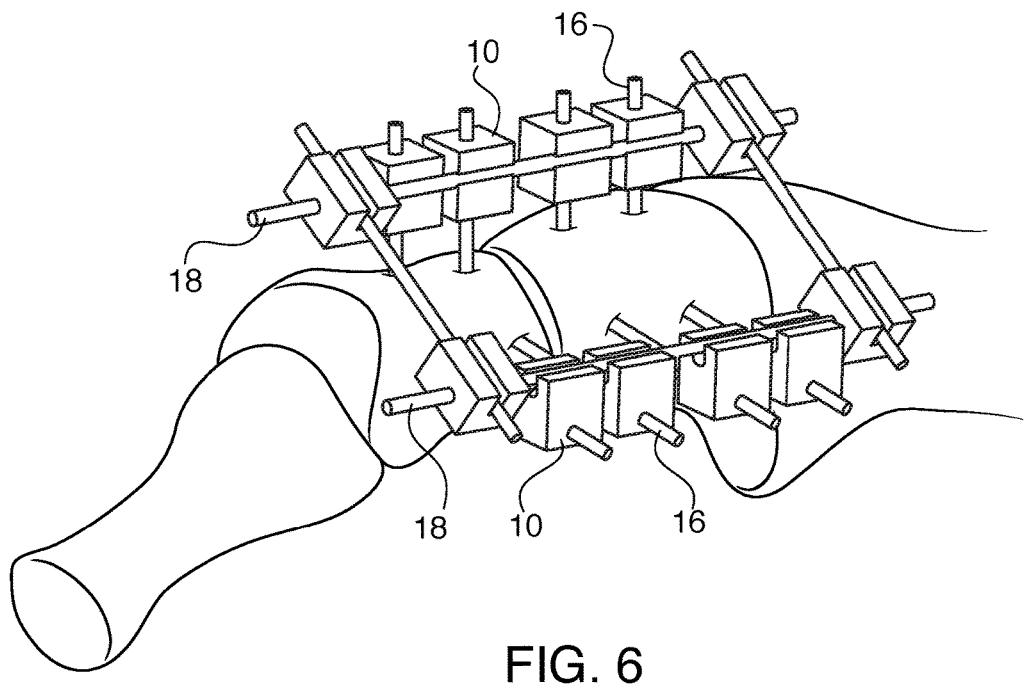
FIG. 6 shows another alternative of the fixation system on a finger.

FIGS. 5 and 6 show alternative embodiments of the system. In FIG. 5, a single rod 18 is used and the needles 16 extend out on only one side of the finger. In the embodiment of FIG. 6, the brackets 10 and rods 18 are disposed at an angle other than 180 degrees to each other, so that the needles 16 extend only through one side of the finger as well, but two different systems are used to stabilize the finger.

Figure 7:
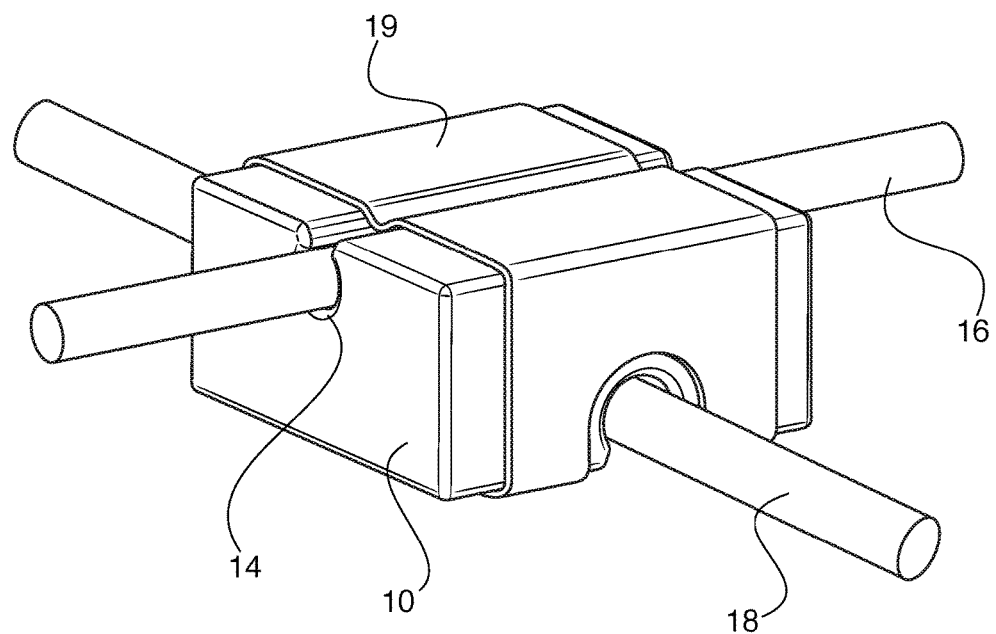
FIG. 7 shows the bracket with a clip for coving the channel.

FIG. 7 shows an alternative embodiment of the bracket 10, where a clip 19 can be used to retain the needles 16 in their respective channels 14. Claim 19 can be snapped into place and held on to bracket 10 via friction fit.

The present invention provides a simple and inexpensive way to connect the needles and fixation rods to stabilize a fracture in a finger. The brackets can be quickly and easily attached to the needles and rods with little movement. This system is ideal for fixing small bones, as the brackets occupy very little space, and are lightweight.

Accordingly, while only a few embodiments of the present invention have been shown and described, it is obvious that many changes and modifications may be made thereunto without departing from the spirit and scope of the invention.

What is claimed is:

1. A fixation system for fixating a fracture in one or more bones of a finger, comprising:
    a plurality of needles adapted to be placed through the bones and extending out of the finger on at least one side of the bones;
    at least one rod configured to extend along at least one side of the finger; and
    a plurality of brackets, each bracket comprising a block having a first channel extending in a first direction and being open to a first surface of the block, and having a second channel extending in a second direction and being open to a second surface of the block,
    wherein the first surface and second surface are located opposite each other,
    wherein the first channel is arranged perpendicular to the second channel, and wherein a width of the channel at each of the first and second surfaces is less than a diameter of the corresponding channel,
    wherein the first channel of each bracket is dimensioned to hold the needles and the second channel of each bracket is dimensioned to hold the at least one rod, such that each of the needles is connected to the rod on at least one end of the needles via the brackets by snapping the needles into the respective first channels and snapping the at least one rod into the respective second channels of the brackets.

2. The fixation system according to claim 1, wherein the plurality of brackets is made of molded polyurethane.

3. The fixation system according to claim 1, wherein there are three needles and three brackets.

4. The fixation system according to claim 1, wherein the at least one rod is made of reinforced carbon fiber.

5. The fixation system according to claim 1, further comprising a clip assigned to at least one of the first and second channels of the bracket, said clip being configured for closing the at least one channel to lock a respective one of the needles or rods in the channel.

6. A method of fixing a broken bone in a finger comprising:
    placing a plurality of needles through the bone such that the needles extend through the finger on at least one side of the bone;
    connecting each of the ends of each of the needles to a bracket comprising a block having a first channel extending in a first direction and being open to a first surface of the block, and having a second channel extending in a second direction and being open to a second surface of the block,
        wherein the first surface and second surface are located opposite each other,
        wherein the first channel is arranged perpendicular to the second channel, and wherein a width of the channel at each of the first and second surfaces is less than a diameter of the corresponding channel,
        wherein the step of connecting comprises snapping each end of each needle into the first channel of the block; and
    connecting the block on one side of the finger to a rod by snapping the rod into the second channel of the block on said one side.

7. The method according to claim 6, wherein the rod is made of reinforced carbon fiber.

8. The method according to claim 7, further comprising applying glue to the rod and needles, or to the channels in the block.

9. The method according to claim 6, further comprising closing a clip over at least one of the channels to lock a respective rod or needle in the respective channel.

* * * * *